United States Patent [19]
Wierzbicki et al.

[11] Patent Number: 5,670,535
[45] Date of Patent: Sep. 23, 1997

[54] NEW THIOPHENE COMPOUNDS

[75] Inventors: Michel Wierzbicki, L'Etang La Ville; Marie-Françoise Boussard, Mareil Sur Mauldre; Jacqueline Bonnet, Paris; Massimo Sabatini, Garges; Philippe Pastoureau, Sevres, all of France

[73] Assignee: Adir et Compagnie, Courbevoie, France

[21] Appl. No.: 618,969

[22] Filed: Mar. 20, 1996

[30] Foreign Application Priority Data

Mar. 21, 1995 [FR] France .................... 95 03246

[51] Int. Cl.$^6$ .................. A61K 31/38; C07D 333/22; C07D 411/06
[52] U.S. Cl. ............... 514/448; 549/72; 544/379
[58] Field of Search ............... 514/448; 549/72; 544/379

[56] References Cited

U.S. PATENT DOCUMENTS

| 3,560,525 | 2/1971 | Kaltenbronn et al. | 260/332.2 |
| 3,960,893 | 6/1976 | O'Mant | 260/332.2 |

FOREIGN PATENT DOCUMENTS

| 0155524 | 2/1985 | European Pat. Off. |
| 0429370 | 11/1990 | European Pat. Off. |

*Primary Examiner*—Mukund J. Shah
*Assistant Examiner*—Sabiha N. Qazi
*Attorney, Agent, or Firm*—The Firm of Gordon W. Hueschen

[57] ABSTRACT

The invention provides new compounds pertaining to the class of: 2-(aminocarbonylalkylcarbonyl)-5-phenylalkylthiophene, enantiomers and physiologically tolerable salts thereof.

For example:

5-[4-(4-methylphenyl)butyl-2-{3,3-dimethyl-4-[N'-(2,3,4-triméthoxybenzyl)-N-piperazinylcarbonyl]butyryl}thiophene is described.

Medicinal products containing the same are useful in the treatment of any pathology involving bone hyper-resorption.

9 Claims, No Drawings

NEW THIOPHENE COMPOUNDS

The present invention relates to new thiophene compounds.

It relates more particularly to thiophene compounds of formula I:

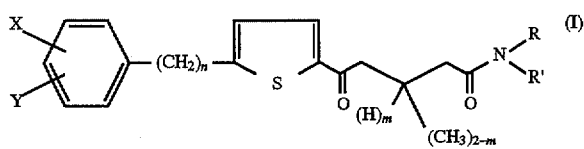

in which:

- each of X and Y, which are the same or different, represents a hydrogen or halogen atom, an alkyl or alkoxy radical each having from 1 to 5 carbon atoms in a straight or branched chain, or a dialkylamino radical in which each alkyl group contains from 1 to 5 carbon atoms in a straight or branched chain;
- n represents an integer from 2 to 5 inclusive;
- m represents zero, one or two;
- R represents a hydrogen atom or an alkyl radical having from 1 to 5 carbon atoms in a straight or branched chain; and
- R' represents an alkyl radical having from 1 to 5 carbon atoms in a straight or branched chain; or
- R and R' form together with the nitrogen atom to which they are bonded a pentagonal or hexagonal heterocyclic radical optionally containing an oxygen atom or a second nitrogen atom, which heterocyclic radical is unsubstituted or substituted by an alkyl radical having from 1 to 5 carbon atoms in a straight or branched chain or by an arylalkyl radical in which the alkyl group contains from 1 to 5 carbon atoms in a straight or branched chain and the aryl group (which is preferably phenyl) is unsubstituted or substituted by one or more identical or different substituents selected from halogen atoms and alkyl and alkoxy radicals each having from 1 to 5 carbon atoms in a straight or branched chain.

When m is 1, the compounds of formula I contain an asymmetric carbon atom and accordingly are in the form of enantiomers which, as such, form part of the present invention.

The compounds of formula I that contain a free amine function (that is to say other than that bonded to the carbonyl group) yield salts with physiologically tolerable acids, which salts, as such, are likewise included in the present invention.

The closest prior art to the present invention is illustrated by European Patent Specification 0 429 370, which relates inter alia to 5-phenylalkyl-2-aminoalkyl-thiophenes of the formula:

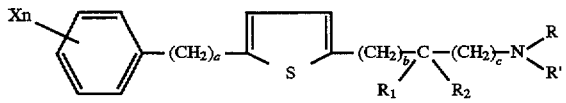

which have bone anti-resorbing activity.

The modifications of structure starting from the said prior-known compounds—and in particular the introduction of two carbonyl groups into the aminoalkyl chain—have led to the compounds of the present invention which, in addition to being new relative to the compounds of the prior art, exhibit considerable pharmacological advantages over those compounds, in particular better water-solubility and an increased anti-resorbing potential, allowing them to be used to achieve the same therapeutic effect with a lesser risk (the hydrophilic nature of the products reducing side-effects especially in the gastro-enterological sphere) and at lower cost (thanks to the use of lower doses).

The present invention relates also to a process for the preparation of compounds of formula I, characterised in that:

an acid of formula II:

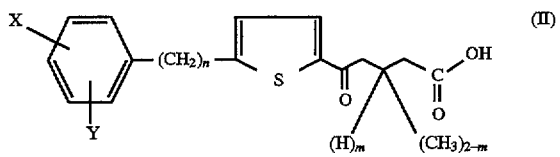

in which X, Y, n and m are as defined above, and an amine of formula III:

in which R and R' are as defined above,
are coupled by means of a coupling agent in a suitable solvent.

It is especially expedient to use carbonyldiimidazole as the coupling agent and to carry out the reaction in methylene chloride.

The amines of formula III used as starting materials are known products.

The acids of formula II used as starting materials are either known or prepared from known substances in accordance with processes used for the synthesis of analogous acids, as indicated in the Examples below.

The compounds of the present invention have valuable pharmacological and therapeutic properties especially on bone metabolism.

In the normal state, bone restructuring allows the anatomical and structural integrity of the skeleton to be maintained. It operates in cycles and depends upon two large types of cell population, the osteoclasts and the osteoblasts. The osteoclasts, after activation, bring about resorption of the old bone by acidification and then enzymatic digestion, handing over, in a successive phase, to the osteoblasts, which form the new osteoid tissue, which will then be calcified. These two metabolic phases—resorption and formation—are closely linked to each other in the physiological state. In a pathological situation, an imbalance may occur between the two phases with, in particular, resorptive hyperactivity leading to excessive bone loss which is insufficiently compensated for by the phase of neoformation. That is the case in particular with postmenopausal osteoporosis, Paget's disease and hypercalcaemia of malignant origin.

The compounds of the present invention have especially valuable pharmacological and therapeutic properties by virtue of their inhibitory activity on bone hyper-resorption, which activity has been demonstrated both in vitro and in vivo, as is shown by the pharmacological study described below in Example 27.

Those pharmacological properties allow the compounds of the present invention to be used in pathologies characterised by bone loss due to resorptive hyperactivity, such as, especially, postmenopausal osteoporosis, Paget's disease and malignant hypercalcaemia.

The present invention relates also to pharmaceutical compositions comprising as active ingredient a compound of formula I or a physiologically tolerable salt thereof, in admixture or in association with a suitable pharmaceutical excipient, such as, for example, glucose, lactose, starch, talc, ethylcellulose, magnesium stearate or cocoa butter. The pharmaceutical compositions so obtained are generally in dosage unit form and may be in the form of, for example, tablets, dragées, gelatin capsules, suppositories, or injectable or drinkable solutions and may be administered orally, rectally or parenterally, as appropriate.

The dosage varies according to the age and weight of the patient, the mode of administration, and associated treatments.

The following Examples illustrate the present invention.

Example 1

5-[4-(4-methylphenyl)butyl]-2-{3,3-dimethyl-4-[N'-(2,3,4-trimethoxybenzyl)- N-piperazinylcarbonyl] butyryl}thiophene

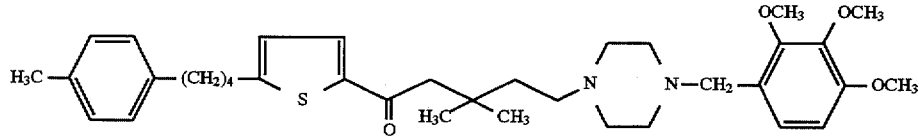

43.3 g (0.116 mol) of 5-[4-(4-methylphenyl)butyl]-3,3-dimethyl-4-{5-[4-(4-methylphenyl)butyl]thien-2-ylcarbonyl}butyric acid (prepared by the method described in European Patent Specification 0 429 370) are dissolved in 200 ml of methylene chloride. There are then added slowly to that solution, which is cooled to 10° C., 26 g (0.16 mol) of carbonyldiimidazole, and the mixture is then allowed to return to room temperature and stirring is carried out until the reaction is complete and the evolution of gas has ceased.

58.81 g (0.22 mol) of N-(2,3,4-trimethoxybenzyl) piperazine in solution in 200 ml of methylene chloride are then added slowly to the reaction mixture. The whole is kept at room temperature, with stirring, for 24 hours and then 500 ml of water are added. After separation, the organic phase is washed in succession with 200 ml of water and then with 2×100 ml of a 0.1N solution of HCl.

The organic phase is then brought to dryness by distillation. The residue is purified by chromatography on silica, using methylene chloride as eluant. The fractions are combined and, after removal of the solvent, the expected product is obtained in the form of an oil.

The base so obtained is dissolved in 100 ml of anhydrous ether, and 30 ml of a 4N solution of HCl in ether are added. The precipitate that forms is filtered off and then taken up in the minimum amount of ethyl acetate. The solution is filtered over a millipore and the filtrate is brought to dryness. The residue is recrystallised from anhydrous isopropanol. In that manner, 50.5 g of 5-[4-(4-methylphenyl)butyl]-2-{3,3-dimethyl-4-[N'-(2,3,4-trimethoxybenzyl)-N-piperazinylcarbonyl]butyryl}thiophene hydrochloride are obtained, m.p.: 96° C.

Examples 2 to 26

By proceeding in the manner described in Example 1, the compounds of the following Examples were prepared:

2) 5-[3-(4-methylphenyl)propyl]-2-{3,3-dimethyl-4-[N'-(2,3,4-trimethoxybenzyl)-N-piperazinylcarbonyl] butyryl}thiophene (oil), the hydrochloride of which melts at 70° C.
3) 5-[3-(4-methylphenyl)propyl]-2-{4-[N'-(2,3,4-trimethoxybenzyl)-N-piperazinyl carbonyl] butyryl}thiophene (oil), the hydrochloride of which melts at 138° C.
4) 5-[3-(4-isopropylphenyl)propyl]-2-{3,3-dimethyl-4-[N'-(2,3,4-trimethoxybenzyl)-N-piperazinylcarbonyl] butyryl}thiophene (oil), the hydrochloride of which melts at 94° C.
5) 5-[2-(4-methylphenyl)ethyl]-2-{3,3-dimethyl-4-[N'-(2,3,4-trimethoxybenzyl-N-piperazinylcarbonyl] butyryl}thiophene (oil), the hydrochloride of which melts at 107° C.
6) 5-[3-(2,5-dimethylphenyl)propyl]-2-{3,3-dimethyl-4-[N'-(2,3,4-trimethoxybenzyl-N-piperazinylcarbonyl] butyryl}thiophene (oil), the hydrochloride of which melts at 89° C.
7) 5-[5-(4-methylphenyl)pentyl]-2-{3,3-dimethyl-4[N'-(2,3,4-trimethoxybenzyl)-N-piperazinylcarbonyl] butyryl}thiophene (oil), the hydrochloride of which melts at 99°–100° C.
8) 5-[3(2,4-dimethylphenyl)propyl]-2-{3,3-dimethyl-4-[N'-(2,3,4-trimethoxybenzyl)-N-piperazinylcarbonyl] butyryl}thiophene (oil), the hydrochloride of which melts at 118° C.
9) 5-[4-(4-methylphenyl)butyl]-2-{3-methyl-4-[N'-(2,3,4-trimethoxybenzyl)-N-piperazinylcarbonyl] butyryl}thiophene (oil), the hydrochloride of which melts at 135° C.
10) 5-[4-(4-methylphenyl)butyl]-2-{4-[N'-(2,3,4-trimethoxybenzyl)-N-piperazinylcarbonyl] butyryl}thiophene (oil), the hydrochloride of which melts at 138°–140° C.
11) 5-[3-(4-methylphenyl)propyl]-2-{3-methyl-4-[N'-(2,3,4-trimethoxybenzyl)-N-pipera zinylcarbonyl] butyryl}thiophene (oil), the hydrochloride of which melts at 118° C.
12) 5-[3-(4-isopropylphenyl)propyl]-2-(3,3-dimethyl-4-diethylaminocarbonyl)butyryl thiophene (oil), ν CO:1643 cm$^{-1}$.
13) 5-[3-(2,5-dimethylphenyl)propyl]-2-(3,3-dimethyl-4-morpholinocarbonylbutyryl) thiophene (oil), ν CO:1644 cm$^{-1}$.
14) 5-[5-(4-methylphenyl)pentyl]-2-(3,3-dimethyl-4-piperidinocarbonylbutyryl)thiophene (oil), ν CO:1644 cm$^{-1}$.
15) 5-[3-(4-isopropylphenyl)propyl]-2-(4-morpholinocarbonylbutyryl)thiophene (oil), ν CO:1652 cm$^{-1}$.
16) 5-[2-(4-methylphenyl)ethyl]-2-{3,3-dimethyl-4-[N'-(2-cyclopentyloxy-3,4-dimethoxy-benzyl)-N-piperazinylcarbonyl]butyryl}thiophene (oil), ν CO of the hydrochloride:1645 cm$^{-1}$, prepared using, as the amine, N-(2-cyclopentyloxy- 3,4-dimethoxybenzyl)piperazine, which was itself prepared by alkylation of N-benzyl-N'-(2-hydroxy-3,4-dimethoxybenzyl)piperazine with bromocyclopentane, followed by catalytic debenzylation.

17) 5-[3-(4-methylphenyl)propyl]-2-(3,3-dimethyl-4-diethylaminocarbonylbutyryl)thiophene (oil), ν CO:1642 cm-¹.
18) 5-[3-(4-isopropylphenyl)propyl]-2-[3,3-dimethyl-4-(N-methyl-N-cyclohexylaminocarbonyl)butyryl]thiophene (oil), ν CO:1643 cm-¹.
19) 5-[3-(2,5-dimethylphenyl)propyl]-2-[3,3-dimethyl-4-(N'-methyl-N-piperazinyl-carbonyl)butyryl]thiophene (oil), the hydrochloride of which melts at 120° C.
20) 5-[5-(4-methylphenyl)pentyl]-2-{3,3-dimethyl-4-[N'-(2,4-dimethoxy-3-propoxybenzyl)-N-piperazinylcarbonyl]butyryl}thiophene (oil), ν CO of the hydrochloride: 1646 cm¹, prepared using, as the amine, N-(2,4-dimethoxy-3-n-propoxybenzyl)piperazine, which was itself prepared by alkylation of N-benzyl-N'-(2,4-dimethoxy-3-hydroxybenzyl)piperazine, followed by catalytic hydrogenation.
21) 5-[3-(2,5-dimethylphenyl)propyl]-2-{3-methyl-4-[N'-(3,4dimethoxy-2-pentyloxybenzyl)-N-piperazinylcarbonyl]butyryl}thiophene (oil), ν CO of the hydrochloride: 1651 cm-¹, prepared using, as the amine, N-(2-n-pentyloxy-3,4-dimethoxybenzyl)piperazine, which was itself prepared by alkylation of N-benzyl-N'-(2-hydroxy-3,4-dimethoxybenzyl)piperazine with 1-bromopentane, followed by catalytic debenzylation.
22) 5-[3-(4-isopropylphenyl)propyl]-2-[4-(N'-methyl-N-piperazinylcarbonyl)butyryl]thiophene (oil), the hydrochloride of which melts at 162° C.
23) 5-[3-(2,5-dimethylphenyl)propyl]-2-[3-methyl-4-(N-methyl-N-cyclohexylaminocarbonyl)butyryl]thiophene (oil), ν CO:1642 cm-¹. 24) 5-[4-(4-methylphenyl)butyl]-2-[3-methyl-4-(diethylaminocarbonyl)butyryl]thiophene (oil), ν CO:1644 cm-¹.
25) (R)-5-[4-(4methylphenyl)butyl]-2-{3-methyl-4-[N'-(2,3,4-trimethoxybenzyl)-N-piperazinylcarbonyl]butyryl}thiophene (oil), the hydrochloride of which melts at 127° C.
26) (S)-5-[4-(4-methylphenyl)butyl]-2-{3-methyl-4-[N'-(2,3,4-trimethoxybenzyl)-N-piperazinylcarbonyl]butyryl}thiophene (oil), the hydrochloride of which melts at 127° C.

The acids of formula II used as starting materials in the synthesis of the products described in the Examples above were prepared as follows.

1—The acids of formula II in which m is either 0 or 2 were prepared by the method described in European Patent Specification 0 429 370 for the synthesis of the compounds of formula (C) of that patent specification.

2—The acids of formula II in which m is 1, which are asymmetric acids, were prepared in the manner described below for the preparation of (R)-5-{5-[4-(4-methylphenyl)butyl]thien-2-yl}-5-oxo-3-methylpentanoic acid

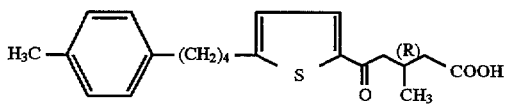

3.45 g (0.015 mol) of 2-[4-(4-methylphenyl)butyl] thiophene are dissolved in 20 ml of tetrahydrofuran. The resulting solution is cooled to −70° C., and then 12 ml of a 1.6M solution of BuLi in tetrahydrofuran are added dropwise thereto. The mixture is allowed to return to 0° C. and is added slowly to a solution of 4.18 g (0.0194 mol) of manganese bromide in 30 ml of tetrahydrofuran at 0° C. The mixture is allowed to return to 20° C., is kept at that temperature for 30 minutes, and is then cooled to −10° C. and added to acid chloride of the formula:

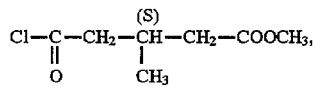

in solution in 10 ml of diethyl ether (which acid chloride has been prepared by adding 2 ml of oxalyl chloride to a solution of 2.4 g (0.015 mol) of methyl (R)-(+)-3-methylmonoglutarate in 2 ml of chloroform, followed by stirring at room temperature for 2 hours and then removal of the volatile fractions).

The reaction mixture is kept at −10° C. for 15 minutes and then at 20° C. for 12 hours. It is hydrolysed with 40 ml of ice-water and 20 ml of normal HCl. After separation and washing with water and then with a 10% solution of NaHCO₃, the ethereal phase is dried over magnesium sulphate. After removal of the ether by distillation in vacuo and chromatography of the residue on silica, using cyclohexane/ methylene chloride (80/20) as eluant, there are obtained 4.2 g of methyl (R)-5-{5-[4-(4-methyl-phenyl)butyl]thien-2-yl}-5-oxo-3-methylpentanoate in the pure state.

The 4.2 g of ester so obtained are dissolved in a mixture of 15 ml of a normal sodium hydroxide solution and 15 ml of ethanol. The solution is heated to reflux and then kept at reflux for 30 minutes, and then the ethanol is removed by distillation under reduced pressure. The aqueous phase is cooled to 0° C. and then acidified with 15 ml of a normal solution of HCl. The precipitate that forms is filtered off and dried. In that manner there are obtained 3.6 g of (R)-5-{5-[4-(4-methylphenyl)butyl]-thien-2-yl}-5-oxo-3-methylpentanoic acid, which is used as such for the subsequent synthesis (analytical sample, m.p.:94° C.).

The corresponding (S) acid was prepared in the same manner starting from methyl (S)-(−)-3-methylmonoglutarate.

EXAMPLE 27

Pharmacological study

The inhibitory activity on bone hyper-resorption of the compounds of the present invention has been demonstrated as follows:

1. In vitro

This activity has been demonstrated on a hyper-resorption test carried out on bone tissue cultures from mice (calvaria), in accordance with a technique based on the method of J. J. Reynolds et al., Calc. Tiss. Res. 4, 339–349 (1970). The compounds tested had a powerful inhibitory effect on hyper-resorption induced by various agents—retinoic acid, PTH.

By way of example, the results obtained on hyper-resorption with retinoic acid with a group of compounds representative of the invention are given in the Table below:

| Compounds | Hyper-resorption with rétinoic acid % d'inhibition of hyper-resorption at a dose of 1 µM |
|---|---|
| Example 1 | 74.2 ± 2.3% |
| Example 3 | 28.3 ± 7.3% |
| Example 4 | 14.3 ± 10.4% |
| Example 7 | 67.6 ± 5.1% |
| Example 9 | 81.5 ± 2.2% |
| Example 10 | 75.1 ± 3.6% |

The IC₅₀s of the compounds of Examples 1, 7 and 9 are 0.50, 0.37 and 0.27 µM, respectively. The activities of the compounds of Examples 25 and 26 are of the same order of magnitude as that of the compound of Example 9.

2. In vivo

This activity has been demonstrated in mice placed in a situation of bone hyper-resorption induced by a powerful arotinoid—Ro 13-6298—in accordance with a method based on the works of U. Treschel et al., J. Clin. Invest. 80, 1679–1686 (1987). For example, when administered by the oral route daily for a period of 5 days, at doses of 0.5 and 1 mg/kg, the compounds of the present invention of Examples 1, 7 and 9 counteract hypercalcaemia following arotinoic hyper-resorption.

Consequently, the compounds of the present invention can be used in the treatment of pathologies characterised by bone loss due to resorptive hyperactivity, such as, especially, postmenopausal osteoporosis, Paget's disease and malignant hypercalcaemia.

We claim:

1. A thiophene compound selected from those of formula I:

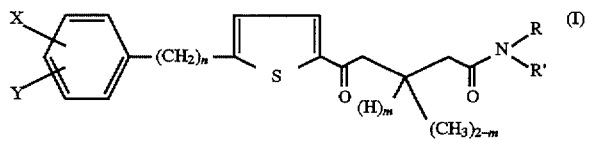

in which:
each of X and Y, which are the same or different, are selected from the group consisting of hydrogen, halogen, alkyl and alkoxy each having 1 to 5 carbon atoms inclusive in straight or branched chains, and dialkylamino in which each alkyl contains 1 to 5 carbon atoms inclusive in straight or branched chains;

n is selected from integers 2 to 5 inclusive;

m is selected from zero, one and two;

R is selected from the group consisting of hydrogen and alkyl having from 1 to 5 carbon atoms inclusive in straight or branched chains; and R' is selected from the group consisting of alkyl having from 1 to 5 carbon atoms inclusive in straight or branched chains, or alternatively R and R' together with the nitrogen to which they are bonded (viz the group

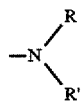

as a whole is selected from the group consisting of: unsubstituted pentagonal and hexagonal heterocycles each selected from those containing one nitrogen, one nitrogen and one oxygen, and two nitrogen, and these heterocycles substituted by a substituent selected from the group consisting of: straight or branched ($C_1$–$C_5$) alkyl and unsubstituted, mono- and poly- substituted arylalkyl in which the alkyl moiety contains 1 to 5 carbon atoms inclusive in straight or branched chains, and the substituent(s) on the aryl moiety is selected from the group consisting of: halogen, straight and branched ($C_1$–$C_5$) alkyl, and straight and branched ($C_1$–$C_5$) alkoxy; and, the corresponding enantiomers, and their addition salts with physiologically-tolerable acids.

2. A compound of claim 1 selected from 5-[4-(4-methylphenyl)butyl]-2-{3,3-dimethyl-4-[N'-(2,3,4-trimethoxybenzyl)-N-piperazinylcarbonyl]butyryl}thiophene and its hydrochloride.

3. A compound of claim 1 selected from 5-[5-(4-methylphenyl)pentyl]-2-{3,3-dimethyl-4-[N'-(2,3,4-trimethoxybenzyl)-N-piperazinylcarbonyl]butyryl}thiophene and its hydrochloride.

4. A compound of claim 1 selected from 5-[4-(4-methylphenyl)butyl]-2-{3-methyl-4-[N'-(2,3,4-trimethoxybenzyl)-N-piperazinylcarbonyl]butyryl}thiophene and its hydrochloride.

5. A compound of claim 1 selected from 5-[4-(4-methylphenyl)butyl]-2-{4-[N'-(2,3,4-trimethoxybenzyl)-N-piperazinylcarbonyl]butyryl}thiophene and its hydrochloride.

6. A compound of claim 1 selected from (R)-5-[4-(4-methylphenyl)butyl]-2-{3-methyl-4-[N'-(2,3,4-trimethoxybenzyl)-N-piperazinylcarbonyl]butyryl}thiophene and its hydrochloride.

7. A compound of claim 1 selected from (S)-5-[4-(4-methylphenyl)butyl]-2-{3-methyl-4-[N'-(2,3,4-trimethoxybenzyl)-N-piperazinylcarbonyl]butyryl}thiophene and its hydrochloride.

8. A method for treating a living animal body afflicted with pathology characterised by bone loss due to resorptive hyperactivity, comprising the step of administering to the living animal body an amount of a compound of claim 1 which is effective for alleviation of said condition.

9. A pharmaceutical composition, useful in the treatment of bone loss, comprising as active ingredient an effective amount of at least one of the compounds according to claim 1 in combination with one or more suitable pharmaceutical excipients.

* * * * *

UNITED STATES PATENT AND TRADEMARK OFFICE
CERTIFICATE OF CORRECTION

PATENT NO. : 5,670,535
DATED : September 23, 1997
INVENTOR(S) : M. Wierzbicki; M-F Boussard; J. Bonnet; M. Sabatini; P. Pastoureau Page 1 of 2

It is certified that error appears in the above-indentified patent and that said Letters Patent is hereby corrected as shown below:

Columns 3 and 4, line 29: The formula should read :

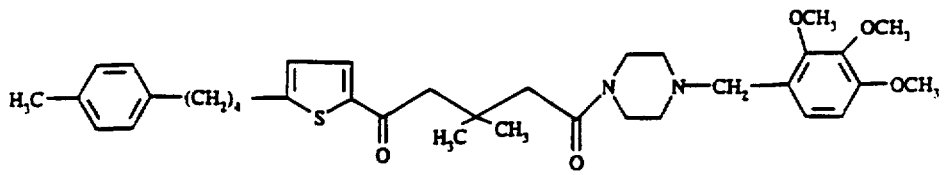

Column 5, line 31: "24) 5-[4-(4-methylphenyl)butyl]-" should begin a new paragraph.

Column 7, line 37: Delete the word "from" between "having" and "1".

Column 7, line 40: Delete "from" at the beginning of the line.

Column 8, line 9: Delete the word "and" at the end of the line and replace with -- or --.

Column 8, line 10: Delete the second instance "and" and replace with the word -- or --.

UNITED STATES PATENT AND TRADEMARK OFFICE
CERTIFICATE OF CORRECTION

PATENT NO. : 5,670,535
DATED : September 23, 1997
INVENTOR(S) : M. Wierzbicki; M-F Boussard; J. Bonnet; M. Sabatini; P. Pastoureau It is certified that error appears in the above-indentified patent and that said Letters Patent is hereby corrected as shown below:

Column 8, line 41: "with pathology" should read -- with a pathology --.

Signed and Sealed this

Thirteenth Day of January, 1998

Attest:

BRUCE LEHMAN

Attesting Officer

Commissioner of Patents and Trademarks